United States Patent [19]
Kraus et al.

[11] Patent Number: 5,734,098
[45] Date of Patent: Mar. 31, 1998

[54] METHOD TO MONITOR AND CONTROL CHEMICAL TREATMENT OF PETROLEUM, PETROCHEMICAL AND PROCESSES WITH ON-LINE QUARTZ CRYSTAL MICROBALANCE SENSORS

[75] Inventors: Paul R. Kraus, Boilingbrook, Ill.; Robert D. McClain; Michael K. Poindexter, both of Sugar Land, Tex.

[73] Assignee: Nalco/Exxon Energy Chemicals, L.P., Sugar Land, Tex.

[21] Appl. No.: 621,402

[22] Filed: Mar. 25, 1996

[51] Int. Cl.$^6$ ................................. G01N 33/00
[52] U.S. Cl. ............................................ 73/61.62
[58] Field of Search .................. 73/24.01, 24.03, 73/24.05, 28.03, 32 R, 32 A, 30.01, 53.01, 53.05, 54.01, 54.41, 61.45, 61.79, 579, 61.62, 61.71; 436/151, 52; 427/10; 310/312

[56] References Cited

U.S. PATENT DOCUMENTS

| | | | |
|---|---|---|---|
| 4,526,480 | 7/1985 | Ward | 374/117 |
| 4,808,538 | 2/1989 | Roffey et al. | 436/6 |
| 5,201,215 | 4/1993 | Granstaff et al. | 73/54.41 |
| 5,208,162 | 5/1993 | Osborne et al. | 436/6 |
| 5,369,033 | 11/1994 | Di Milia et al. | 436/148 |
| 5,416,448 | 5/1995 | Wessendorf | 331/116 R |
| 5,484,626 | 1/1996 | Storjohann et al. | 427/8 |
| 5,487,981 | 1/1996 | Nivens et al. | 435/30 |
| 5,571,945 | 11/1996 | Koutrakis et al. | 73/28.03 |

OTHER PUBLICATIONS

Sandia National Laboratories: a)Acoustic Resonator Microsensor Increases Throughput, Reduces Waste b) In Situ Fluid Monitor Meets Automotive and Industrial Needs c) Acoustic Wave Sensor Provides Compact, Low Cost Chemical Detection d) Portable Sensor Systems Monitor Pollutants, Other Chemicals e) Fiber Optics Technology Enables New Chemical Contaminant Sensor f) New Hydrogen Sensor is Small, Rugged, and Inexpensive g) Pattern Recongnition Provides Rapid Economical Chemical Indentification U.S. Department of Energy Multiprogram Laboratory.

"The Level Oscillator for Use in High Resistance Resonator Applications" Kurt O. Wessendorf, 1993, U.S. Department of Energy, Sandia Labs.

"Sensing Liquid Properties with Thickness–Shear Mode Resonators", S. J. Martin, G.C. Frye, K.O. Wessendorf – *Sensors and Actuators* A 44 (1994) 209–218.

"Effect of Surface Roughness on the Response of Thickness–Shear Mode Resonators in Liquids", S. J. Martin, G. C. Frye, A. J. Ricco, S. D. Senturia, Reprinted form *Analytical Chemistry*, 1993, 65; pp. 2910–2922.

"Characterization of a Quartz Crystal Microbalance with Simultaneous Mass and Liquid Loading", *Analytical Chemistry*, 1991, 63, 2272–2281.

"Quartz Crystal Microbalance Jet Fuel Test System" Sandia National Laboratories.

"Studies of Jet Fuel Thermal Stability and Oxidation Using a Quartz Crystal Microbalance and Pressure Measurements" S. Zabarnick, Ind. Eng. Chem. Res. 1994, 33, 1348–1354.

"Studies of Jet Fuel Additives using the Quartz Crystal Microbalance and Pressure Monitoring at 140C", S. Zabarnick and R. R. Grinstead, Univ. of Dayton Res. Inst.

"Studies of Jet Fuel Thermal Stability and Autoxidation Using a Quartz Crystal Microbalance", S. Zabarnick & B. Grinstead *Symposium on Distillate Fuel Auto–Oxidation Chemistry*; 207th National Mtg. Amer. Chem. Soc. Mar. 13–18, 1994.

"Advanced Diagnostics for In Situ Measurement of Particle Formation and Deposition in Thermally Stressed Jet Fuels", T. J. O'Hern, W. M. Trott, S. J. Martin, E. A. Klavetter, *31 Aerospace Sciences Mtg. & Exhibit* Jan. 11–14, 1993/Reno NV.

"Monitoring Jet Fuel Thermal Stability Using a Quartz Crystal Microbalance", E. A. Klavetter, S. J. Martin, K. O. Wessendorf *Energy & Fuels* 1993, 7, 582–588.

"Cloud Point Determination Using a Thickness Shear Mode Resonator", J. J. Spates, S. J. Martin, A. J. Germer, pp. 492–496.

"Quartz Resonator Fluid Monitors for Vehicle Applications", R. W. Cernosek, S. J. Martin, K. O. Wessendorf, M. D. Terry, A. N. Rumpf Sandia Natl. Labs. *Proceedings of the Sensors Expo*, Cleveland, OH, Sep. 20–22, 1994, pp. 527–539.

"In Situ Coking Kinetics Obtained from a New Flow Through Microbalance and Reaction Kinetics Monitored by GC", S. C. Fung, C. A. Quernini, K. Liu, D. S. Rumschitzki, T. C. Ho. *Catalyst Deactivation 1994*, pp. 305–312.

"A Piezoelectric Biosensor for Listeria Monocytogenes", M.B. Jacobs, R.M. Carter, G.J. Lubrano, G. G. Guilbault, *American Laboratory*, Jul. 1995, pp. 26–28.

"An Ultrasensitive Fouling Monitoring System for Cooling Towers", Y. Nohata, H. Taguchi, *Environmental Effects*, Mar. 1995, pp. 43–46.

*Primary Examiner*—Hezron E. Williams
*Assistant Examiner*—Richard A. Moller
*Attorney, Agent, or Firm*—Robert A. Miller; Kelly L. Cummings

[57] ABSTRACT

Thickness-shear mode resonators which simultaneously measure mass deposition and fluid properties can be utilized to monitor petroleum processing, petrochemical and water treatment systems. Specialty chemical additive materials can be accurately and instantaneously added to control conditions detected by the thickness-shear mode resonators. The thickness-shear mode resonators are piezoelectric crystals used in conjunction with oscillator circuitry that can determine mass as well as viscosity and/or density of a fluid in contact with the piezoelectric surface.

25 Claims, No Drawings

METHOD TO MONITOR AND CONTROL CHEMICAL TREATMENT OF PETROLEUM, PETROCHEMICAL AND PROCESSES WITH ON-LINE QUARTZ CRYSTAL MICROBALANCE SENSORS

INTRODUCTION

The addition of specialty chemicals to a multitude of industrial processes is desirable and often required for efficient, profitable, and safe operation of the processes. The addition of specialty chemical treatments to such processes can help to reduce process fouling, corrosion, and foaming, among other things. These treatment chemicals are added to the processes at concentrations ranging from parts-per-billion to percent levels. The treatment dosage is often determined by monitoring changes in process parameters that correspond to the addition of the specialty chemical over time. Optimally, those skilled in the art desire to relate dosage to changes in the process fluids. However, the means for determining dosage is often very time consuming as vital process parameters will many times only change meaningly over a very long time period. For some processes, the appropriate determination of the correct specialty chemical dosage can take several months. Once established, these dosages are set to a static value. The dosage does not increase or decrease as the fouling, corrosion, or foaming rate, for example, changes over time. This results many times in the addition of a wasteful excess of specialty chemical or worse, undertreatment with the specialty chemical.

Examples of methods used to control the addition of specialty chemicals include the use of coupon analyses, off-line residual product testing, residual polymer testing, on-line pH monitors, conductivity monitors, and the like. However, these methods, and many others that have been utilized to monitor performance and control dosage are typically slow and not indicative of real-time changes in the process. Residual testing, for example, typically involves removing a sample fluid from the process and subjecting the sample for analyses at some site away from the process. Also, in the case of on-line meters like pH probes and conductivity meters, the detection limit and variance of many methods is too high to provide accurate data for the control of the addition of specialty chemicals. That is, the sensitivity of on-line instrumentation is often not high enough to enable an operator to adjust the dosage of specialty chemical in real-time. Thus, for the precise and accurate control of the addition of specialty chemicals to industrial processes, a highly sensitive, in situ method that provides real-time feedback on the state of fluids in a process is desirable.

The use of quartz crystal microbalances to measure the amount of scaling, deposit formation or mass loss occurring in both hydrocarbon and aqueous systems is known. These devices operate by exciting a quartz crystal in contact with fluid (liquid or vapor) to a resonant frequency and then measuring the shift in resonant frequency due to the loss or accumulation of mass from/on the crystal surface. While successful in measuring the mass of deposits of hard, crystalline scale or foulant, we have found that traditional quartz crystal microbalance units are an unreliable indicator of many types of phenomena that occur in both aqueous and non-aqueous systems. In the first place, traditional quartz crystal microbalances do not accurately measure the mass of amorphous deposits formed from, for instance, biofouling, or the deposits of amorphous hydrocarbons on the surfaces of processing units or the like. Relying on traditional quartz crystal microbalances for these types of measurements produces inaccurate and unreliable data that cannot be used to control the feed of chemical used to correct a condition that is being measured.

Examples of the use of typical quartz crystal microbalances for the measurement of crystalline scale formation in aqueous systems is found in co-pending United States patent application, Ser. No. 08/421,206 filed Apr. 13, 1995, the disclosure of which is hereinafter incorporated by reference into this specification. While the device and methods described in Ser. No. 421,206 operates accurately, and gives excellent control when only crystalline scale is formed in a system, we have found that this device does not work in systems where amorphous, or combinations of amorphous and crystalline scale may form. Further, devices such as that described in Ser. No. 421,206 cannot be used to sense changes that occur in a fluid, such as a viscosity increase or decrease, density increase or decrease, the presence of an immiscible fluid, or the growth of an amorphous precipitate forming in the interior of a container containing a fluid.

Accordingly, this invention utilizes a method for the measurement of the properties of materials and process streams, and more particularly the measurement of the viscosity and density of materials, and more particularly to the accurate and rapid measurement of the viscosity and density of aqueous and non-aqueous fluids as well as mass deposition. The method of this invention employs a thickness-shear mode resonator device to determine mass accumulation, viscosity, and/or density of hydrocarbon solutions, vapors, and mixtures as well as mass accumulation, viscosity, and/or density of aqueous fluids. By the utilization of this method, rapid, precise measurements can be obtained, instantaneously as well as over time, that can be used to control the addition of treatment chemicals and process variables in the system. By the use of the thickness-shear mode resonator device, the processing of crude oils and chemicals can be greatly improved by the proper and timely addition of antifoulants, by improved emulsion breaking in both waste water treatment and crude oil demulsification as well as breaking emulsions formed in the processing of crude oil (e.g., desalting, demulsification, and certain emulsions that are formed in the processing of hydrocarbons, for instance in ethylene furnace quench towers), by the proper addition of dispersants or other additives to hydrocarbons, and by the addition of finished product biocide control chemicals or stabilizers. Likewise, the thickness-shear mode resonator devices may be used in aqueous systems to measure the growth and/or deposit of biological, inorganic, or organic scales, or the devices may be utilized to measure the rate at which corrosion is occurring in either an aqueous or a hydrocarbon system. Additional uses of the thickness-shear mode resonator devices are disclosed hereinafter.

BACKGROUND

Quartz crystal microbalances, also sometimes called piezoelectric sensors, have been suggested for measuring the mass of matter depositing from a fluid medium, measuring the viscosity of a flowing fluid, determining the rate at which films are deposited, monitoring corrosion, and the like. While somewhat successful, quartz crystal microbalances measuring only shifts in resonant frequency often gave erroneous readings when used in industry under certain conditions. For instance, quartz crystal microbalances which were excellent at the measurement of hard adherent scale which actually deposited on the crystal and dampened the vibration of the crystal, often did not give proper results when amorphous or soft scale (biological growth, amorphous inorganic crystals, and the like) were deposited on the same crystal. This is because the devices relied only upon measuring shifts in resonant frequency. Therefore, these sensors would be useless as a means to control the addition of treatment chemicals like biocides and antipolymerants.

Thickness-shear mode resonators useful in the practice of this invention are known to those in the art. A particularly useful thickness-shear mode resonator is disclosed in Granstaff et. al U.S. Pat. No. 5,201,215 the disclosure of which is hereinafter incorporated by reference into this specification. This device is able to determine the density-viscosity product of a given fluid. It should be pointed out that the quartz crystal portion of this thickness-shear mode resonator is substantially identical to the quartz crystal microbalances of the prior art. It is the manner in which the signal is processed which renders the use of the Granstaff thickness-shear mode resonators unique, and which allows these thickness-shear mode resonators to do what typical quartz crystal microbalances cannot do. What differentiates the thickness-shear mode resonators useful in this invention from quartz crystal microbalances which cannot be utilized to measure the density-viscosity of a given fluid is the oscillator circuitry. The oscillator circuitry of the device described in Granstaff '215 provides not only a measure of resonant frequency, but also a measure of changes in resonant frequency amplitude which is sensitive to the physical properties of the fluid medium in which the crystal is immersed.

A second type of thickness-shear mode resonator which is useful in the practice of this invention is disclosed by S. J. Martin et al. in *Sensors and Actuators* A 44 (1994) 209–218 the disclosure of which is also hereinafter incorporated by reference into this specification. This type of device utilizes a first sensor having a toughened surface and a second sensor having a smooth surface. By the use of this device it has been found possible to simultaneously determine and resolve mass deposition, fluid, viscosity and density. By using both smooth and rough surfaces which respond differently to mass adhesion, it is possible to differentiate mass deposition and viscosity and density of a fluid in contact with the piezoelectric crystal of the thickness-shear mode resonator.

As stated in Granstaff '215, the mass of a solid and/or the physical properties of a fluid may be determined when both the mass and the fluid contact the same quartz crystal by applying an oscillating electric field across the thickness of the quartz crystal microbalance in contact with a solid mass interposed between the quartz crystal microbalance and a fluid, measuring at least one resonant frequency of the quartz crystal microbalance, simultaneously measuring the admittance magnitude at the resonant frequencies, and correlating the resonant frequency and the admittance magnitude to obtain a surface mass density and a fluid viscosity-density product.

Alternatively, and as also taught by Granstaff, an oscillating electric field may be applied across the thickness of a quartz crystal microbalance, sweeping a frequency over a range that spans at least one resonant frequency of the crystal, measuring the magnitude and phase of the admittance over the frequency range, correlating the admittance data to the frequency, and applying admittance/frequency correlation to an equivalent circuit model, contacting a solid mass and/or a fluid onto the crystal wherein the solid mass is interposed between the crystal and the fluid, repeating the steps of sweeping the frequency range that spans a resonant frequency, measuring the magnitude and phase of the admittance over that frequency range, and correlating the admittance data to the frequency and then applying the admittance/frequency correlation to the equivalent circuit model and then extracting the solid mass and fluid density-viscosity product from the correlated admittance/frequency data.

While Granstaff et al. discloses that the mass layer may be metals, metal alloys, salts, some rigid polymers, or ice, and that these solids may be applied to the quartz crystal microbalance by evaporation, electroplating, precipitation, or other chemical or thermodynamic reaction, there is no appreciation by Granstaff et al. that the method may be effectively utilized in the field of hydrocarbon processing or water treatment, or that the devices may be effectively utilized to control the addition of process additives in these areas.

We have found however that a certain type of quartz crystal microbalance, substantially as described in Granstaff, can be used to overcome the disadvantages of the prior art quartz crystal microbalance units, and can supply accurate and instantaneous data for the control of the feed of chemicals used to control or modify both aqueous and non-aqueous processes.

It is therefore an embodiment of this invention to provide to the art a method for the control of chemical additives into hydrocarbon processing and water treatment processes through the use of thickness-shear mode resonator devices.

It is a further embodiment of this invention to provide to the art an accurate and real-time method for the control of the feed of chemical additives into hydrocarbon processing and water treatment processes.

It is a still further embodiment of this invention to provide to the art an accurate and real-time method for the control of the feed of condition correcting chemical additives into hydrocarbon processing and water treatment processes.

Additional embodiments of this invention will appear hereinafter.

THE INVENTION

The basic method of this invention involves the use of the thickness-shear mode resonator device, installing such device in a location where the quartz crystal surface of the device can be in contact with a fluid which as used herein may be a liquid or vapor (gas), measuring both a mass and a fluid viscosity-density output, determining the condition of the system, and adding treatment chemical, or taking such other corrective action as the mass and fluid viscosity-density outputs dictate. The thickness-shear mode device may be installed on the surface of a container for such fluid, or may simply be inserted into the fluid. Where the device is inserted into the fluid on either a temporary or permanent basis care should be taken to insure that an accurate representation of the fluid contacts the surface of the quartz crystal. The thickness-shear mode resonator device is preferably inserted on the surface of a container holding the fluid. The use of the word container is meant to include piping, tanks, or any other device which contains a fluid.

The invention is applicable to the determination of the properties of both aqueous and non-aqueous systems. Among the principle uses for this invention are the determination of scaling, corrosion, and biofouling in aqueous systems, the determination of organic fouling and corrosion in hydrocarbon processes, and determination of the rate of break of both water-in-oil and oil-in-water emulsions, the determination of fluid characteristics such as viscosity, density, percent: solids, and the like, the amount of sedimentation occurring in a tank or vessel and the rate at which such sedimentation occurs. As stated, these are only some of the applications of the invention in the fields of water treatment and hydrocarbon processing.

By the use of the term water treatment herein is meant the prevention of inorganic scale, corrosion, and biofouling on the surfaces in contact with a water supply or industrial water system. The invention as stated above is particularly useful in the determination of the rate of biological growth occurring in an aqueous system. Also included in the term water treatment as used herein is the separation of solids from fluids, either vapor or liquid, using either chemical and/or mechanical means, and the separation of oil from water, again, using either chemical and/or physical means. As used herein the term hydrocarbon processing means the transport of crude oil by pipeline, rail, barge, or tanker, and the processing of this crude oil into useful products by various means including desalting processes, distillation, cracking, and other means to produce salable products, as well as the further treatment of such hydrocarbon products in the chemical processing industries including the production of such valuable materials as styrene, butadiene, isoprene, vinyl chloride, ethylene, propylene, acrylonitrile, acrylic acid, alkyl acrylates, and the resultant polymeric materials formed from such materials. In practice, the subject invention may be employed in any situation where it is desired to know the rate at which organic foulants are formed on the surfaces of heat transfer equipment, flow lines, storage tanks, and the like. The thickness-shear mode resonator may be installed to achieve the method of the subject invention at any location in a process where organic fouling, inorganic scaling, corrosion, or microbiological growth can be expected, or where a change in the characteristics of a fluid may indicate a processing problem which can be corrected through the addition of a chemical treatment. Likewise the subject invention can be utilized to determine the rate at which emulsions can be broken, or the condition of an emulsion in real time so as to allow the feeding of an appropriate emulsion breaking (or conversely, if an emulsion is the desired product, an emulsifier) material. Because the use of this invention allows for real-time data, control over scaling, fouling, microbiological growth and the like is rapidly and accurately achieved in an unprecedented manner. The inventors herein know of no other technique that can simultaneously provide instantaneous, real-time mass deposition and fluid property data to control the feed of water treatment chemicals and/or hydrocarbon processing treatment chemicals.

In one of its broadest senses, the invention is a method for the determination of a fluid condition occurring on the surface of a container containing such fluid, and instantaneously or subsequently taking steps to correct such condition which method comprises the steps of:

A. placing a thickness-shear mode resonator device into the container, and placing the quartz surface of the thickness-shear mode resonator device into contact with the fluid;

B. continuously exciting the thickness-shear mode resonator device and measuring the frequency shift and damping voltage components of the thickness-shear mode resonator device output;

C. continuously determining the condition of the surface of the thickness-shear mode resonator device based on the frequency shift and damping voltage components; and then, D. continuously correcting the condition detected on the surface of the thickness-shear mode resonator device by taking an action from the group consisting of:

i. activating or deactivating a chemical feed pump applying a condition correcting chemical to the fluid;

ii. increasing the flow of fluid out of the system; or, iii. decreasing the flow of fluid out of the system.

While the frequency shift and damping voltage components which are the output of the thickness-shear mode resonator can be used directly, it is oftentimes useful to convert this data to mass and a viscosity-density component. As stated above, the thickness-shear mode resonator device may be placed adjacent to the surface of the container holding the fluid or may be inserted into the container in any location where the fluid contained in the container is in contact with the quartz crystal surface of the thickness-shear mode resonator device. The container utilized may be advantageously selected from the group consisting of hydrocarbon processing units, hydrocarbon storage tanks, pipelines, or transport vessels such as barges, ships, and railcars.

Additionally, while the thickness-shear mode resonator device of the invention may be placed into the system on a permanent basis, it is also possible to place such a device into a system on a temporary basis to determine whether a fluid condition correcting chemical should be added.

While useful in the correction of a condition on a surface in contact with a fluid, the invention may also be utilized to control a condition of the fluid itself in either a liquid or gaseous state, and regulate a condition of the fluid such as consistency, viscosity, and the like. In one of its broadest senses, the invention involves the determination of a fluid condition in a fluid manufacturing process, including the storage or transport of said fluid, and instantaneously taking steps to correct such condition which steps comprise:

A. inserting into the container containing said fluid a thickness-shear mode resonator device whereby the quartz surface of the thickness-shear mode resonator device is in contact with the fluid;

B. continuously exciting the thickness-shear mode resonator device and measuring the frequency shift and damping voltage components of the thickness-shear mode resonator device output;

C. continuously determining the condition of the surface of the thickness-shear mode resonator device based on the frequency shift and damping voltage components; and then, D. continuously correcting the condition detected on the surface of the thickness-shear mode resonator device by taking an action from the group consisting of:

i. activating or deactivating a chemical feed pump applying a condition correcting chemical to the fluid;

ii. increasing the flow of fluid out of the system; or, iii. decreasing the flow of fluid out of the system.

To state the invention in another manner, the basic invention of this application operates in a water treatment system by using the following steps:

A. inserting into the water, preferably on the surface the container containing such water, a thickness-shear mode resonator device whereby the quartz surface of the thickness-shear mode resonator is in contact with the industrial water;

B. continuously exciting the thickness-shear mode resonator device and measuring the mass and viscosity-density components of the thickness-shear mode resonator device output;

C. continuously determining the condition on the surface of the thickness-shear mode resonator device based on the mass and viscosity-density components; and then, D. continuously correcting the condition detected on the surface of the thickness-shear mode resonator device by taking an action from the group consisting of:
  i. activating or deactivating a chemical feed pump applying a condition correcting chemical to the industrial water system;
  ii. increasing the flow of water out of the system; or,
  iii. decreasing the flow of water out of the system.

While in the above description the term thickness-shear mode resonator device has been used in the singular form it is often times desirable to use more than one thickness-shear mode resonator device in a given system. As such, the singular form of the term thickness-shear mode resonator is used herein to include herein one, two, or multiple thickness-shear mode resonator devices. This allows for additional control of the system. The use of multiple thickness-shear mode resonator devices is especially important when the devices are used to determine sediment in a tank, emulsion breaking efficiency, the level of foam in a vessel, the level of each of two or more distinct phases in a container, and the like.

The use of this invention allows for the real-time determination of parameters which effect the aqueous system. By the use of this method, scale formation, corrosion, or biological fouling can be detected long before such scale, corrosion, or biological fouling can be visually detected in the system, and long before other methods of measurement would provide the same information. Because of the sensitivity of thickness-shear mode resonators, problems occurring in the system are detected much earlier than with traditional methods, and corrective action through the use of appropriate scale or corrosion inhibitors or microbiocides can be initiated immediately to control the problem. Through the rapid control of the system by the methods of this invention, superior control of industrial systems can be achieved. By the use of the thickness-shear mode resonator devices in the subject method, exacting control of aqueous water treatment systems can be accomplished. The thickness-shear mode resonator also operates in real-time which avoids problems with basing chemical feed on coupon analyses which are composite (integrated over time) sampling. This type of monitoring does not indicate upset conditions as they occur.

In a non-aqueous system, for example a hydrocarbon processing unit, the invention could, on a real-time basis determine a fouling, corrosion and/or biological growth condition occurring on the surface of a hydrocarbon processing unit in contact with the hydrocarbon fluid (either a liquid or gas) contained in the hydrocarbon processing unit, and steps could instantaneously be taken to correct such condition. These steps include:
A. placing a thickness-shear mode resonator device into the fluid contained in the hydrocarbon processing unit, whereby the quartz surface of the thickness-shear mode resonator is in contact with the hydrocarbon;
B. continuously exciting the thickness-shear mode resonator device and measuring mass and viscosity-density components;
C. continuously determining the condition of the surface of the thickness-shear mode resonator based on the mass and viscosity-density components; and then,
D. continuously correcting the condition detected on the surface of the thickness-shear mode resonator by activating or deactivating a chemical feed pump applying a condition correcting chemical to the hydrocarbon processing unit.

Again, because of the sensitivity of the subject method, fouling and scaling can be detected at extremely low levels, and corrective action taken instantaneously, and therefore before major problems occur. As stated above, while the thickness-shear mode resonator device is preferably placed on the surface of the hydrocarbon processing unit so that the quartz crystal of the thickness-shear mode resonator is in contact with the fluid, in this inventions broadest sense, it is only important that the quartz crystal surface of the thickness-shear mode resonator device be in contact with the fluid to be measured. Through the use of the method of the invention it would be expected that major problems like the deposition of asphaltenes on the surface of a heat transfer device in a refinery could be noted before they became serious or even life threatening such as the occurrence of a runaway, exothermic polymerization in a monomer storage tank. It is noted that these are examples of the method of the invention only, and those skilled in the art of hydrocarbon processing, both in the production and treatment of crude oil, refining, and the production of petrochemicals will readily see other areas in which this invention can be utilized. The hydrocarbon processing equipment in which the method of this invention is applicable include almost any equipment processing a crude oil, or distillate to manufacture fuels, or petrochemical products. The equipment may be a compressor, reboiler, heat exchanger, purification column, hold vessel, or reactor. Likewise the invention is applicable to almost any hydrocarbon processing unit including those processing alkenes and alkynes (e.g. ethylene, propylene, styrene, acrylonitrile, acrylic acid, alkyl acrylates, vinyl chloride, butadiene, and isoprene) as well as downstream units that further process the alkenes and alkynes. Chemical additives that may be controlled include scale and corrosion inhibitors, antifoulants, antifoams, antipolymerants, and the like. It will be readily apparent that this invention is not limited to any specific type of specialty chemical additive to any particular process.

The invention may also be used to determine the viscosity, density or a viscosity/temperature condition of a hydrocarbon fluid contained in a container and instantaneously taking steps to correct or modify such condition. Steps used include:
A. inserting a thickness-shear mode resonator into the container holding such hydrocarbon whereby the quartz surface of the thickness-shear mode resonator device is in contact with the hydrocarbon;
B. continuously exciting the thickness-shear mode resonator device and measuring mass and viscosity-density components;
C. continuously determining the condition of the hydrocarbon fluid based on the mass and viscosity-density components; and then,
D. continuously correcting the condition of the hydrocarbon fluid by activating or deactivating a chemical feed pump applying a condition correcting chemical to hydrocarbon fluid contained in said container.

This process is useful, for example, in the processing of diesel fuels or other fuel which requires the addition of a pour point depressant to maintain adequate fluidity, or such other additive such as a viscosity index improper, or other additive which changes the characteristic of the hydrocarbon fluid. Likewise, as in aqueous systems, the invention may also be useful for detecting the occurrence and level of foaming in a process, and may be useful in the introduction of anti-foams into a processing system.

The invention may also be useful in the application of emulsion breakers (or conversely emulsifiers) to oil-in-water or water-in-oil emulsions such as that produced in the treatment of slop oil, refinery desalters, waste water treatment, or the like. In this method typically two or more thickness-shear mode resonator devices of the invention are placed at varying levels in the vessel in which the emulsion is located. The differing characteristics of the fluids, generally encompassing two or more immiscible fluids can be read using the thickness-shear mode resonators and data accumulated on the status of the emulsion at any particular level in such vessel or tank. Because of the differing viscosity and density of water, and oil, and any intermediate rag layer, the progress of emulsion breaking can be followed, and deemulsifier can be added as a result of mass, viscosity, and density determinations made through the use of the thickness-shear mode resonators. The method for determining the condition of a hydrocarbon/aqueous fluid mixture and the feed of emulsion breaker to such a system generally comprises the following steps:

A. inserting into the container holding or containing the hydrocarbon/aqueous fluid mixture a thickness-shear mode resonator device whereby the quartz surface of the thickness-shear mode resonator device is in contact with the hydrocarbon/aqueous fluid mixture;

B. continuously exciting the thickness-shear mode resonator device and measuring mass and viscosity-density components;

C. continuously determining the condition of the hydrocarbon/aqueous fluid mixture based on the mass, viscosity and density components; and then, D. continuously correcting the condition of the hydrocarbon/ aqueous fluid mixture by activating or deactivating a chemical feed pump applying a condition correcting chemical to the processing unit containing the hydrocarbon/aqueous fluid mixture.

While this embodiment can be practiced using only one thickness-shear mode resonator placed at a level in the container at which it is desired to measure which phase is present, it is oftentimes useful to utilize two or more thickness-shear mode resonators located at differing levels of the container or tank to determine the status of the fluid at each of the measured levels. In a most preferred mode of practicing this embodiment of the invention, at least two devices are employed, one of which is preferably located at a location to detect the presence of an aqueous phase, and at least one of such devices positioned at a location to detect the presence of a hydrocarbon phase. An additional device may be used at a level where the "rag" or surface interface between the two immiscible fluids occurs. The hydrocarbon/ aqueous fluid mixture to be treated is generally contained in a container selected from the group consisting of crude oil demulsification vessels, crude oil heater treaters, crude oil desalting units, ethylene quench water towers, dilution steam generating systems, hydrocarbon storage tanks, hydrocarbon transport vessels, waste water clarifiers, waste water treatment units, settling tanks, accumulators, and metal working fluid sump. The use of more than one thickness-shear mode resonator gives operators of emulsion breaking processes instantaneous, real-time information on the status of the emulsion and control of the feed of condition correcting deemulsifier or other chemical to the emulsion. The term mixture as used in the sense above is meant to include water-in-oil emulsions, oil-in-water emulsions, emulsion "rag" layers, separated oil layers, and separated water layers, as well as dispersions of solids in liquids.

While this method has been described as being useful for the breaking of emulsions, of course the method may also be used in the formation of emulsions. By using density-viscosity readings obtained by the thickness-shear mode resonator devices, emulsifying agent can be added to produce an emulsion having desired characteristics.

As may be seen, each of the embodiments of the invention described herein takes advantage of the thickness-shear mode resonator. In the use of the thickness-shear mode resonator to determine the quantity of scale, fouling and/or corrosion occurring, the thickness-shear mode resonator is mounted so that the exposed side of the quartz is in direct contact with the fluid circulating in the system. In designing such systems, it is important to take into account the fluid turbulence caused by the insertion of the thickness-shear mode resonator. Accordingly, when measuring fouling, scaling, corrosion, or even the viscosity or other characteristic of a fluid, it is often advantageous to mount the thickness-shear mode resonator flush with the surface of the container or pipe through which the fluid passes. When a flush mounting is not practical, or where the thickness-shear mode resonator cannot be installed flush with the surface of the container or pipe through which the fluid passes, those skilled in the art will readily determine the best location for the thickness-shear mode resonator. In all installations, it is critical that the exposed portion of the quartz surface of the thickness-shear mode resonator contact the fluid being measured, or the fluid from which scale or fouling is being deposited.

In yet another embodiment of the invention, a portable thickness-shear mode resonator could be utilized. In its simplest form, the portable fixture would be easily inserted into the fluid or head space of a tank, drum, or open vessel.

The quartz crystal surface of the thickness-shear mode resonator of the invention can be as small as desired, or as large as practical. Quartz crystal microbalances of the type required to build the thickness-shear mode resonators useful in the practice of the subject invention are available in various sizes from a variety of commercial sources. One of the features of this invention is that the thickness-shear mode resonator allows for the rapid and accurate determination of a condition and the change in a parameter to control the condition. The invention is usable over a wide variety of pressures and temperatures. When used at under high pressures, it is preferred that both sides of the quartz crystal be pressure equalized. When only one side of the crystal is subjected to high pressure, distortion of the crystal may take place causing inaccurate readings. Likewise, the invention is useful over a wide range of temperatures ranging from substantially below freezing to as high as the melting point of the electrical connections used to receive the signal from the quartz crystal. As such, while the device is not directly useful in the pyrolysis section of for instance an ethylene furnace, the device is usable at points exiting the furnace.

Among the many uses of the thickness-shear mode resonator is when such device controls the addition of a specialty chemical material which is designed to ameliorate or otherwise moderate a condition, for example the mining on or off of a pump containing microbiocide, corrosion inhibitor, scale inhibitor, fouling inhibitor, or the like. Methods for the development of circuits controlling pumps using the output of the thickness-shear mode resonator device are well known in the art. Such circuits use the signal, after the determination through calibration of a desired signal level from the thickness-shear mode resonance device, to drive such pump means. In addition to driving a pump means, the signal can also be utilized to open or close blow-down valves in the case of a cooling water or boiler water system, or to increase or decrease the flow of a hydrocarbon fluid passing through a given system, increase or decrease the residence time of an emulsion contained within a vessel that is necessary for breaking such emulsion, or the like.

In the operation of the thickness-shear mode resonators useful in the subject invention, an oscillator circuit is utilized to maintain a constant potential across a piezoelectric crystal (quartz crystal) to provide stable oscillations. The output is measured and processed in accordance with the general principles elucidated in U.S. Pat. No. 5,201,215 previously incorporated by reference herein.

While it is a current preferred mode of utilizing our invention to use the calculated mass and viscosity-density results obtained by processing the raw data generated by the Granstaff device, the "raw-data" output, frequency shift and damping voltage, obtained by using the circuitry described in Granstaff, and elsewhere in Wessendorf U.S. Pat. No. 5,416,448, the disclosure of which is hereinafter incorporated by reference into this specification, is also a measure of the changes occurring on the sensor surface and may be used directly without conversion to physical property values. This technique may be especially useful where it is difficult to obtain accurate mass or fluid property results. In those applications, the chemical additive could be controlled by empirical observation of the frequency and/or voltage output.

This raw data is also of course a measurement of the viscosity-density and mass components of the fluid in contact with the piezoelectric device, and our invention encompasses the control of specialty chemical processes using either the raw frequency shift and voltage data, or the viscosity-density and mass components calculated from the raw data.

EXAMPLES

Acrylonitrile is typically recovered from the gaseous effluent of catalytic reactors by extraction with water in a column typically known as an absorber. Hydrogen cyanide and acrylonitrile are selectively extracted from the effluent and this mixture is boiled overhead in a recovery column to a set of towers where the acrylonitrile is isolated as a pure component by a series of distillations. Residual organics in the flow from the bottom of the recovery column are removed by distillation in the stripper column and most of the remaining water is sent back to the absorber in this cyclic recovery process. Efficient operation of the recovery process is limited by fouling that occurs in the process, especially on heat transfer equipment like reboilers, heat exchangers and distillation towers. This problem can be alleviated by the addition of commercially available specialty chemical antifoulants. Application of antifoulant material to the process at dosages from 0.001–1000 ppm may significantly slow the rate of process fouling and subsequently extend unit run lengths, reducing the number of periodic equipment cleanings, and increase unit throughput. The application rates of antifoulant to units of this type are now based on laboratory testing, or empirical data on the number of days a unit can be left on-line with a given antifoulant dosage. In actual practice, if the heat exchanger run length is too short because of the existence of fouling, antifoulant dosage is increased until an acceptable run length is obtained, or no fouling is evident. This process often leads to the overdose of antifoulant because the antifoulant dosage is maximized for the worst possible condition and is not based on actual fouling conditions in the unit. There exists no in situ, on-line, real-time method to determine optimum dosage of antifoulant.

In order to monitor the dosage of antifoulant, a quartz crystal sensor of the type described herein would be installed in critical locations in the acrylonitrile purification process. Typical locations at which thickness-shear mode resonators would be installed would include the solvent water stream just prior to a heat exchanger. This sensor would be installed so as to protrude into the solvent water stream. The crystal would be driven by an oscillator circuit on the outside pipewall. Oscillator and crystal would be connected via a hermetic rf circuit on the outside pipewall. The oscillator would provide a frequency and an amplitude output. Changes in resonant frequency would be indicative of changes in mass on the crystal surface and/or changes in fluid properties. Changes in amplitude are reflective of crystal damping. The measurements of crystal damping could be an especially useful measurement because damping is affected by the viscoelastic nature of the deposit, and the deposits in an acrylonitrile process can be highly viscoelastic. Viscoelastic deposits in the acrylonitrile process would preclude the use of other quartz crystal microbalance sensors that fail to account for the influence of viscoelastic properties. Damping is also important to resolve changes in mass from changes in fluid properties since resonant frequency is sensitive to each. Traditional quartz resonator sensors would not satisfy this requirement since these devices are sensitive to changes in resonant frequency only. The sensor used herein is useful in controlling the process because the associated oscillator circuit is sensitive to changes in resonant frequency and changes in amplitude (damping voltage).

In the sensor placed in the solvent water line, oscillator output would be measured by a frequency meter and a voltmeter that were each connected to a personal computer. Other measurements collected would include time and temperature. Using output from the oscillator, the computer would be used to calculate and plot the rate of mass accumulation on the crystal surface. This rate would then be determined prior to the injection of antifoulant to the process, and the deposition rate in the untreated solvent water would be proportional to the rate of fouling in the heat exchanger. This rate would be continually monitored over time as antifoulant was injected into the system. The antifoulant dosage would then be adjusted until the rate began to change. This would be manifested on the computer by a change in slope for the line that results from a plot of deposited mass versus time. Eventually the antifoulant dosage could be slowly adjusted until the slope of this line approached zero (no detectable deposition over a given time interval) to obtain an optimized antifoulant dosage. The optimized dosage would be established by actual real-time measurement rather than indiscriminate variables that are easily affected by other process parameters. At any time during the run, if deposition increased, the antifoulant rate would be increased to compensate for the higher fouling rate.

As an alternative to placing the thickness-shear mode resonator in the solvent water stream, a small slip stream taken from the acrylonitrile recovery process could be utilized. In some cases it would be expected that overall deposition of solids in the bulk solvent water would overwhelm the thickness-shear mode resonators. To attenuate large flow rates and fouling rates, a small flow of solvent water would be diverted to a flow cell containing the thickness-shear mode resonator. Deposition of solids from the slip stream would be proportional to deposition from the bulk solvent water provided that process parameters like temperature and pressure were maintained at constant levels. To facilitate these conditions, the flow cell may be heated by means such as heater rods, heat tape, steam, or other conventional means. Furthermore, the addition of a back pressure regulator to the slip stream line to maintain a constant pressure could also be useful. In this case, the thickness-shear mode resonator in the flow cell would be attached to an oscillator circuit outside of the flow cell and slip stream tubing. The oscillator output would be used as above to calculate the deposition rate and optimize antifoulant feed.

As will be readily apparent to those skilled in the art, a microprocessor could be substituted for components like the voltmeter and frequency meter. The microprocessor would make the devices more convenient to work with and would allow the use of data loggers and laptop computers. Output of the microprocessor in this case would be interfaced with the laptop computer or datalogger. In yet another possible variation, the computer would be used to automatically control the pumpstroke on a pump adding antifoulant to the acrylonitrile process. The computer would be programmed to adjust pumpstroke by a certain degree for a proportional change in the rate of solid deposition on the crystal surface. When the fouling rate drops to zero, the computer would direct the pump to hold constant at its present pumpstroke or to reduce pumpstroke by a certain percentage. In this manner, chemical antifoulant dosage would be automatically optimized.

The thickness-shear mode resonator would also be useful in the control of antifoulants to other hydrocarbon processing operations. As a further example, this hypothetical example discloses the use of the thickness-shear mode resonator to control antifoulant addition to the caustic wash system of an ethylene plant.

In an ethylene plant so called acid gases like carbon dioxide and hydrogen sulfide are removed from the hydrocarbon mixture by washing the gaseous hydrocarbon with an aqueous caustic solution. This is normally done at a location in the process called a caustic tower. The caustic tower is prone to fouling due to the base catalyzed polymerization of reactive aldehydes like acetaldehyde. Fouling in the caustic tower and associated equipment can be controlled by the application of commercially available antifoulants. In most situations, there is no convenient manner of determining the optimum dosage of antifoulant required to reduce fouling to an acceptable level or to eliminate fouling. In some instances which have not been satisfactory, attempts have been made to set antifoulant dosage based on the amount of acetaldehyde that is fed to the caustic tower. In one possible configuration, the thickness-shear mode resonator would be installed in the tower bottom fluids. Detection of solids in the tower bottoms would be indicative of the amount of foulant formed during washing of the hydrocarbon gas. Response from the sensors would be used to set the optimum dosage of caustic tower antifoulant required to eliminate fouling in the caustic tower. The detection of little, or no solids in the flow from the tower bottoms would determine the optimum antifoulant dosage.

The hypothetical examples below describe the use of the thickness-shear mode resonator to control fouling in the processing of light hydrocarbon streams.

During the recovery of light hydrocarbons in ethylene plants, butadiene plants, isoprene plants and the like, distillation towers and associated equipment like heat exchangers and reboilers are fouled by the thermal and/or oxidative polymerization of reactive olefins like butadiene. By placing the thickness-shear mode resonator devices useful in this invention into the vapor space, beneath select trays in the tower, the probes could be used to detect the formation of foulant from the vapor phase. Traditionally this is a very difficult problem to detect until the polymeric foulant, often called "popcorn polymer", has damaged hardware within the tower. Popcorn polymer grows from the vapor phase on the metal surfaces in the tower. Thickness-shear mode resonators may be placed in the vapor space of towers such as primary fractionators, depropanizers, debutanizers, and butadiene purification columns. The thickness-shear mode resonators would be sensitive to the formation of viscoelastic polymer in the vapor phase which would deposit on the resonators. The deposition of a thin, viscoelastic film of foulant would be detectable using the oscillator circuitry described above. If formation of foulant on the crystal was detected, then the dosage of vapor phase antifoulant could be adjusted accordingly. In this way, the exact amount of antifoulant required to control vapor phase fouling could be determined.

Hydrocarbon recovery towers also foul in the liquid and gaseous phases. Placing the thickness-shear mode resonators described above into the liquid tower bottoms would help to detect solids that deposit in the tower bottoms and in associated reboilers. These sensors could be used to control the amount of antifoulant that is added to the tower bottoms and to the reboilers. These additives are usually different from those added to control vapor phase fouling although the foulant is usually similar, a viscoelastic polymer that is insoluble in the liquid hydrocarbon.

Sometimes foulant is brought into a tower from another source. Consider the addition of pyrolysis gasoline to a primary fractionator. In some cases, spent caustic is washed with pyrolysis gasoline to remove benzene from the spent caustic prior to disposal of the spent caustic. After the pyrolysis gasoline is separated from the caustic, the pyrolysis gasoline is sometimes used as reflux in the primary fractionator. During the washing of the spent caustic, aldol polymer is formed by the caustic-catalyzed polymerization of phenylacetaldehyde and other reactive carbonyl species in the pyrolysis gasoline. Any soluble gum formed in this process is carried to the primary fractionator, where some of the gum precipitates onto hardware within the primary fractionator. Accumulation of gum in the primary fractionator would lead to a fouled tower. Pyrolysis gasoline from benzene strippers have been found to contain as much as 1 gram of gum per 100 mL gasoline. Commercially available dispersants can be added to the gasoline to help control the deposition of the gum in the primary fractionator. The placement of the thickness-shear mode resonator devices of the subject invention in the process lines returning reflux to the tower could be used as an indication of the amount of gum in the pyrolysis gasoline reflux. Response from the sensors could be used to determine the appropriate dosage of antifoulant required to keep gum dispersed in the tower. Not only would the sensors respond to the deposition of gum onto the crystal surface, but they would also respond to the changes in viscosity of the pyrolysis gasoline due to higher or lower concentrations of soluble gum in the liquid.

As stated above, the thickness-shear mode resonator can be used for monitoring the growth of biofilm or "soft" deposits which cannot be measured using previously known quartz crystal microbalance devices. Among the applications in aqueous systems that can be monitored using the thickness-shear mode resonator include pulp and paper processes where microbiological growth presents a problem, cooling water systems where bacteria and algae growth can present significant problems and certain waste treatment systems. The invention may also represent an improved method in waste water emulsion breaking, the separation of an oil phase from a water phase, and other systems in which the different densities of liquids can be detected by the thickness-shear mode resonator device. Because the thickness-shear mode resonator device can simultaneously measure mass loading and fluid property changes such as density and viscosity in contrast to the earlier known device circuits, side stream sampling using the thickness-shear mode devices can be accurately used to monitor a microbiological fouling event in real time. The output of the thickness-shear mode resonator is directly related to the growth of the biofilm and may be used to control a chemical feed pump: Appropriate control algorithms may be developed which will ensure that the film growth rate remains within acceptable limits. Without thickness-shear mode resonance devices, coupon sampling is the only direct measurement technique available. Coupon sampling, however, requires obtaining a composite sample over a period of time and does not report system upsets as they occur. Real-time monitoring afforded by the thickness-shear mode resonator will enable these upsets to be rapidly controlled by changing the chemical treatment dosage.

Likewise, within a cooling tower, there is simultaneous mineral scale deposition and micro-biological fouling. The ability to measure and to differentiate these two modes of fouling would enable a cooling tower treatment program to be optimized. The thickness-shear mode resonator described herein, and as set forth in U.S. Pat. No. 5,201,215, describes an instrument that simultaneously measures mass accumulation and changes in fluid density-viscosity product. The differentiation of these two properties will allow proper dosing of both anti-scale treatment chemicals and biocide treatments to be optimized.

The ability to measure sample viscosity on-line would enable real-time control of the addition of viscosity modifiers for slurries. Viscosity modifiers are added to slurries used in precious metals processing to reduce energy consumption by pumping equipment. The method of the present invention would enable on-line control of the addition of these treatment chemicals using sampling and control techniques described above.

As an example, a thickness-shear mode resonator would be installed on the wall of a paper machine in contact with the furnish being used. The thickness-shear mode resonator would be calibrated to respond to an increase in biofilm mass occurring on the surface of its quartz crystal. Upon the deposit of a biofilm onto the surface of the quartz crystal, the thickness-shear mode resonator would send a signal indicative of the build up of biofilm. This signal would be amplified, and a pump feeding a water soluble microbiocidal product would be started. The feed of biocide would continue so long as the mass of deposit would increase, and would stop when the mass of deposit either decreased or held constant. In similar fashion, the viscoelastic properties of the biofilm can also be used to monitor biofilm fouling. By using either method, the paper machine would be kept substantially free of biological growth. Because of the sensitivity of the thickness-shear mode resonator, the microbiocide would be added at a rate required to reduce biological growth and reduce over-feeding the chemical. This would result in reduced chemical consumption.

A thickness-shear mode resonator would be installed on the interior wetted wall of an industrial cooling tower. The thickness-shear mode resonator would be calibrated to indicate mass deposition on its surface, and the signal would be amplified and would be connected to a pump connected to a supply of commercially available industrial microbiocide. The pump would feed biocide material into the cooling tower. Upon noting microbiological growth, as evidenced by changes in the mass or viscoelastic properties of the sample, the thickness-shear mode resonator would send a signal indicating build up, triggering the pump and initiating the feed of biocide. Upon noting no further buildup or a decrease in buildup, biocide feed would be terminated. By using the system, a cleaner cooling tower would be obtained, and less biocide would be consumed and discharged over time.

The examples presented herein are not intended to be all inclusive of all of the various applications which the sensors of the invention may be employed. Those skilled in the art will readily determine that in addition to determining the rate of fouling of hydrocarbon systems and controlling such fouling, the sensors may also be utilized for such diverse applications as determining the rate at which an emulsion breaks in a desalter and the resultant real-time control of emulsion breaker feed, the rate at which microbiocide should be fed to finished products, and the rate at which chemical treatment should be applied to a hydrocarbon stream to maintain its fluidity and prevent fouling.

Having thus described our invention, we claim:

1. A method for the rapid determination of a scaling, corrosion or biological growth condition occurring on a surface in contact with an industrial water contained in an industrial water system, and for taking steps to correct such condition which comprises the steps of:
   a. inserting a thickness-shear mode resonator device into the industrial water whereby the quartz surface of the thickness-shear mode resonator device is in contact with the industrial water;
   b. continuously exciting the thickness-shear mode resonator device and measuring the output of the thickness-shear mode resonator device as the mass and viscosity-density components of the industrial water in contact with the thickness-shear mode resonator device;
   c. continuously determining the condition of the industrial water contacting the quartz surface of the thickness-shear mode resonator device based on the mass and viscosity-density components of said industrial water; and then,
   d. continuously correcting the condition of said industrial water in contact with the quartz surface of the thickness-shear mode resonator device by taking an action from the group consisting of:
      i. activating or deactivating a chemical feed pump applying a condition correcting chemical to the industrial water;
      ii. increasing the flow of water out of the system; or,
      iii. decreasing the flow of water out of the system.

2. The method of claim 1 wherein the industrial water system is a cooling tower.

3. The method of claim 1 wherein the condition monitored in the industrial water in contact with the quartz surface of the thickness-shear mode resonator device is biofouling, and the chemical feed pump adds a microbiocide or toxicant into the industrial water.

4. The method of claim 1 wherein the industrial water system is an industrial boiler.

5. The method of claim 1 wherein the condition of the industrial water monitored is selected from the group consisting of inorganic scaling, corrosion, and biofouling, and the chemical feed pump adds one or more treatment chemicals selected from the group consisting of water soluble scale inhibitors, biocides, and corrosion inhibitors.

6. The method of claim 1 wherein the quartz surface of the thickness-shear mode resonator device is mounted flush with the surface of the industrial water system through which the industrial water passes and the quartz surface of the thickness shear-mode resonator device is in contact with the industrial water.

7. The method of claim 1 wherein the quartz surface of the thickness-shear mode resonator device is inserted into the industrial water system on a temporary basis.

8. A method for the rapid determination of a fouling, corrosion, scale, or biological growth condition occurring on the surface of a hydrocarbon processing unit in contact with a hydrocarbon fluid and for taking steps to correct such condition which comprises the steps of:

A. placing a thickness-shear mode resonator device into the fluid contained in the hydrocarbon processing unit whereby the quartz surface of the thickness-shear mode resonator device is in contact with the hydrocarbon;

B. continuously exciting the thickness-shear mode resonator device and measuring the output of the thickness shear-mode resonator device as the mass and viscosity-density components of the hydrocarbon fluid in contact with the thickness shear-mode resonator device;

C. continuously determining the condition of the hydrocarbon fluid contacting the quartz surface of the thickness-shear mode resonator based on the mass and viscosity-density components of said fluid; and then, D. continuously correcting the condition of the hydrocarbon fluid contacting the quartz surface of the thickness-shear mode resonator by activating or deactivating a chemical feed pump applying a hydrocarbon fluid condition correcting chemical to the hydrocarbon processing unit.

9. The method of claim 8 wherein the hydrocarbon processing unit is a compressor, reboiler, heat exchanger, purification column, hold vessel, or reactor and the chemical feed pump applies a fouling inhibitor.

10. The method of claim 8 wherein the hydrocarbon processing unit is selected from the group consisting of hydrocarbon processing units producing alkenes and alkynes, and the chemical feed pump applies one of more ingredients from the group consisting of fouling inhibitors, corrosion inhibitors, and antifoams.

11. The method of claim 10 wherein the thickness-shear mode resonator device is placed on the surface of the hydrocarbon processing unit.

12. The method of claim 8 wherein the hydrocarbon processing unit is selected from the group consisting of hydrocarbon processing units producing styrene, acrylonitrile, acrylic acid, alkyl acrylates, vinyl chloride, butadiene, and isoprene.

13. The method of claim 12 wherein the thickness-shear mode resonator device is placed flush with the surface of the hydrocarbon processing unit and the quartz surface of the thickness-shear mode resonator device is in contact with the hydrocarbon fluid contained in the hydrocarbon processing unit.

14. The method of claim 8 wherein the hydrocarbon processing unit processes crude oil and the chemical feed pump applies one or more hydrocarbon fluid correcting chemicals from the group consisting of fouling inhibitors, corrosion inhibitors, scale inhibitors, and antifoams.

15. The method of claim 8 wherein the quartz surface of the thickness-shear mode resonator device is placed flush with the surface of the hydrocarbon processing unit and the quartz surface of the thickness-shear mode resonator device is in contact with the fluid contained in the hydrocarbon processing unit.

16. The method of claim 8 wherein the quartz surface of the thickness-shear mode resonator device contacts the fluid contained in the hydrocarbon processing unit on a temporary basis.

17. A method for the rapid determination of a viscosity-density or viscosity/temperature condition of a hydrocarbon fluid and for taking steps to correct or modify such condition which comprises the steps of:

A. inserting a thickness-shear mode resonator device into the hydrocarbon fluid whereby the quartz surface of the thickness-shear mode resonator device is in contact with the hydrocarbon fluid;

B. continuously-exciting the thickness-shear mode resonator and measuring the output of said thickness shear-mode resonator device as the mass and viscosity-density components of the hydrocarbon fluid;

C. continuously determining the condition of the hydrocarbon fluid in contact with the quartz surface of the thickness-shear mode resonator based on the mass and viscosity-density components; and then, D. continuously correcting the condition of the hydrocarbon fluid by activating or deactivating a chemical feed pump applying a condition correcting chemical to hydrocarbon fluid.

18. The method of claim 17 wherein the hydrocarbon fluid is contained in a container selected from the group consisting of a hydrocarbon processing unit, hydrocarbon storage tank, pipeline, or transport vessel.

19. The method of claim 18 wherein the thickness-shear mode resonator device is placed into the container holding such hydrocarbon fluid on a temporary basis.

20. The method of claim 18 wherein the thickness-shear mode resonator device is placed flush with the surface of the container holding such hydrocarbon fluid and the quartz surface of the thickness-shear mode resonator device is in contact with such hydrocarbon fluid.

21. A method for the rapid determination of the condition of a hydrocarbon/aqueous fluid mixture contained in a container, and for taking steps to correct or modify such condition which comprises the steps of:

A. inserting into the hydrocarbon/aqueous fluid mixture at least one thickness-shear mode resonator device whereby the quartz surface of the thickness-shear mode resonator device is in contact with the hydrocarbon/aqueous fluid mixture;

B. continuously exciting the thickness-shear mode resonator device and measuring the output of the thickness shear-mode resonator as the mass and viscosity-density components of the hydrocarbon/aqueous fluid mixture;

C. continuously determining the condition of the hydrocarbon/aqueous fluid mixture based on the mass and viscosity-density components of said hydrocarbon/fluid mixture; and then, D. continuously correcting the condition of the hydrocarbon/aqueous fluid mixture by activating or deactivating a chemical feed pump applying a condition correcting chemical to the hydrocarbon/aqueous fluid mixture.

22. The method of claim 21 wherein the hydrocarbon/aqueous fluid mixture is contained in a container selected from the group consisting of crude oil demulsification vessels, crude oil heater treaters, crude oil desalting units, ethylene quench water towers, dilution steam generating systems, hydrocarbon storage tanks, hydrocarbon transport vessels, waste water clarifiers, waste water treatment units, settling tanks, accumulators, and metal working fluid sumps.

23. The method of claim 22 wherein the quartz surface of the thickness-shear mode resonator device is inserted flush with the surface of the container containing such hydrocarbon/aqueous fluid mixture and the quartz surface of the thickness-shear mode resonator device is in contact with such hydrocarbon/aqueous fluid mixture.

24. The method of claim 22 wherein the quartz surface of the thickness-shear mode resonator device is inserted into the hydrocarbon/aqueous fluid mixture on a temporary basis.

25. The method of claim 21 wherein two or more thickness-shear mode resonator devices are utilized with at least one of such devices being positioned at a location to detect the presence of an aqueous phase and at least one of such devices being positioned at a location to detect the presence of a hydrocarbon phase.

* * * * *